United States Patent [19]

Falk

[11] Patent Number: 4,490,304
[45] Date of Patent: Dec. 25, 1984

[54] PERFLUOROALKYL THIOALKYLENE AMPHOTERIC COMPOUNDS

[75] Inventor: Robert A. Falk, New City, N.Y.

[73] Assignee: Ciba-Geigy Corporation, Ardsley, N.Y.

[21] Appl. No.: 454,211

[22] Filed: Dec. 29, 1982

[51] Int. Cl.$^3$ .................. C07C 141/02; C07C 141/16; C07C 143/14; C07C 101/02
[52] U.S. Cl. .................. 260/457; 260/453 RY; 260/458 R; 260/458 C; 260/458 F; 260/501.12; 260/929; 260/945
[58] Field of Search ........ 260/458 F, 458 R, 453 RY, 260/501.12, 945, 929, 458 C, 457; 564/285, 292

[56] References Cited
U.S. PATENT DOCUMENTS 4,098,811 7/1978 Falk .................. 260/501.12
4,102,916 7/1978 Falk .................. 260/458 F

OTHER PUBLICATIONS

Cooke et al., C. A., 91, 194,960k (1979).

Primary Examiner—Nicky Chan
Attorney, Agent, or Firm—Michael W. Glynn

[57] ABSTRACT

The perfluoroalkyl thioalkylene amphoteric compounds having the structures:

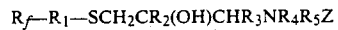

$$R_f-R_1-SCH_2CR_2(OH)CHR_3NR_4R_5Z$$

where $R_f$ is a perfluoroalkyl, $R_1$ is alkylene or alkyleneoxy or aminoalkylene, $R_2$ and $R_3$ are hydrogen, alkyl, or together form a cyclic ring, $R_4$ and $R_5$ are hydrogen or alkyl unsubstituted, or substituted by an anionic function, Z is alkylene substituted by an anionic function, and the acid adduct, alkaline salt or alkyl quaternary ammonium salts thereof, which can be prepared from perfluoroalkylepoxides and amino acids. These compounds are useful as surfactants.

3 Claims, No Drawings

PERFLUOROALKYL THIOALKYLENE AMPHOTERIC COMPOUNDS

BACKGROUND OF INVENTION

Amphoteric sulfonate surfactants containing hydroxyl groups and derived from non-fluorochemical epoxides are described in U.S. Pat. No. 3,480,666, Ger. Off. No. 1,815,863, and Fr. No. 1,571,832, namely

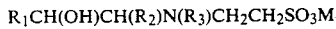
$R_1CH(OH)CH(R_2)N(R_3)CH_2CH_2SO_3M$

Fluorinated amphoteric surfactants derived from certain fluorinated epoxides are described in Jap. No. 8,105,897; namely

$R_f-Y-NR(CH_2)_mC(OH)R'CHR''NR_1R_2R_3W^-$ wherein Y is $-SO_2-$ or $-CO-$.

U.S. Pat. No. 4,038,195 describes fluorinated amphoteric surfactants derived from unsaturated glycicyl ethers of the type

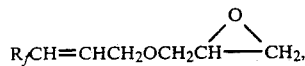
$R_fCH=CHCH_2OCH_2CH{-}{-}CH_2$, namely

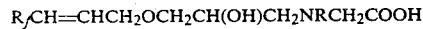
$R_fCH=CHCH_2OCH_2CH(OH)CH_2NRCH_2COOH$ wherein R is hydrogen or methyl.

U.S. Pat. No. 4,283,533 describes amphoteric hydroxybetaines from pentahydroperfluoroalkylamines.

Other non-hydroxyl group containing fluorinated amphoteric compounds are described in U.K. patent application GB No. 2,018,759 A, namely

$R_fANR_1(CH_2)_mNR_2R_3(CH_2)_nCO_2^-$ wherein A is alkylene or substituted alkylene.

Others are described in Brit. No. 1,377,303, U.S. Pat. Nos. 4,188,307, 4,099,594, 4,089,804, 4,069,158, and 3,963,776.

DETAILED DISCLOSURE

This invention is directed to perfluoroalkyl alkylene and thioalkylene hydroxyl containing amphoteric compounds. These compounds are useful as surface active agents.

The fluorine containing amphoteric compounds have the general formula

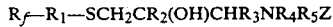
$R_f-R_1-SCH_2CR_2(OH)CHR_3NR_4R_5Z$ wherein $R_f$ is straight or branched chain perfluoroalkyl of 6 to 12 carbon atoms or said perfluoroalkyl substituted by perfluoroalkoxy of 2 to 6 atoms;

$R_1$ is branched or straight chain alkylene of 2 to 8 carbon atoms, alkylenethioalkylene of 2 to 8 carbon atoms, alkyleneoxyalkylene of 2 to 8 carbon atoms or alkyleneiminoalkylene of 2 to 8 carbon atoms where the nitrogen atom contains hydrogen, alkyl of 1 to 6 carbon atoms as a third substituent;

$R_2$ and $R_3$ are independently hydrogen or lower alkyl from 1 to 6 carbon atoms, lower alkoxy-loweralkyl, halo-loweralkyl, cycloalkyl of 5 to 6 carbon atoms and alkenyl of up to 6 carbon atoms or when taken together with or without a sulfur or oxygen hetero atom, contain up to 6 alkylene carbon atoms;

$R_4$ and $R_5$ are independently hydrogen or straight or branched chain alkyl of 1 to 12 carbon atoms or phenyl which are unsubstituted or substituted by carboxy, sulfo, sulfato, phosphoro or phosphono;

Z is straight or branched chain alkylene of 1 to 12 carbon atoms which is substituted by carboxy, sulfo, sulfato, phosphoro, or phosphono, or thiosulfato and the acid adduct, alkaline salt, or N-lower alkyl or N-benzyl quaternary ammonium salts thereof.

Preferred compounds are those where:

$R_f$ is straight or branched chain perfluoroalkyl of 6 to 12 carbon atoms or said perfluoroalkyl substituted by perfluoroalkoxy of 2 to 6 atoms;

$R_1$ is branched or straight chain alkylene of 2 to 8 carbon atoms, alkylenethioalkylene of 2 to 8 carbon atoms, alkyleneoxyalkylene of 2 to 8 carbon atoms or alkyleneiminoalkylene of 2 to 8 carbon atoms where the nitrogen atom contains hydrogen or alkyl of 1 to 6 carbon atoms as a third substituent;

$R_2$ and $R_3$ are hydrogen;

$R_4$ and $R_5$ are hydrogen, methyl, or lower alkyl substituted by carboxy;

Z is alkylene of 1 to 3 carbon atoms substituted by carboxy or sulfo; and the acid adduct, alkaline salt or N-lower alkyl quaternary ammonium salts thereof.

Particularly preferred are those compounds where:

$R_f$ is perfluoroalkyl of 6 to 12 carbon atoms;

$R_1$ is alkylene of 2 to 4 carbon atoms;

$R_2$ and $R_3$ are hydrogen;

$R_4$ and $R_5$ are hydrogen or methyl, or lower alkyl substituted by carboxy;

Z is alkylene of 1 to 3 carbon atoms substituted by carboxy or sulfo; and the acid adduct, alkaline salt or N-lower alkyl quaternary ammonium salts thereof.

The novel $R_f$-amphoterics are obtained by the addition of $R_f$-epoxides of the structure

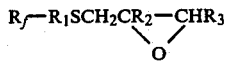
$R_f-R_1SCH_2CR_2-CHR_3$
$\phantom{R_f-R_1SCH_2C}\backslash\;\;/$
$\phantom{R_f-R_1SCH_2CR}O$ to amino acids of formula

$NR_4R_5Z$ where $R_4$, $R_5$ and Z are defined above.

By "lower" is meant those organic radicals having up to 6 carbon atoms, preferably up to 4 carbon atoms. Most preferred lower alkyl includes methyl and ethyl.

Where $R_2$ and $R_3$ together represent a heterocyclic moiety, preferred such groups include morpholino, piperidino, and thiomorpholino.

The acid adducts advantageously include the adducts of conventional inorganic acids, especially the adducts of hydrochloric, hydrobromic, sulfuric, nitric and carbonic acids, and the conventional organic acids, including the lower alkanoic, lower alkylsulfonic, arylcarboxylic, preferably benzoic, and arylsulfonic, preferably tolysulfonic, acids.

Alkaline salts include those of the alkali metals, alkaline earth metals, ammonium and amines, especially lower alkylamines and lower alkanolamines.

The intermediate fluorochemical epoxides useful for this invention are of the general formula:

wherein $R_f$ is straight or branched chain perfluoroalkyl of 6 to 12 carbon atoms or said perfluoroalkyl substituted by perfluoroalkoxy of 2 to 6 atoms;

$R_1$ is branched or straight chain alkylene of 2 to 8 carbon atoms, alkylenethioalkylene of 2 to 8 carbon atoms, alkyleneoxyalkylene of 2 to 8 carbon atoms or alkyleneiminoalkylene of 2 to 8 carbon atoms where the nitrogen atom contains hydrogen alkyl of 1 to 6 carbon atoms as a third substituent;

$R_2$ and $R_3$ are independently hydrogen or lower alkyl from 1 to 6 carbon atoms, alkoxyalkyl, haloalkyl, cycloalkyl and alkenyl or when taken together with or without a sulfur or oxygen hetero atom, contain up to 6 carbon atoms.

The epoxides contain a thioether linkage and when $R_1$ is $-CH_2CH_2-$, and $R_2$ and $R_3$ are H have been disclosed by Blochl in Ger. Off. No. 2,018,461 (1970). Other thio containing epoxides can be made similarly from mercaptans of formula $R_f-R_1-SH$ as disclosed in U.S. Pat. Nos. 3,655,732, and 4,102,916. The epoxides wherein $R_1$ is $-CH_2CH_2-$ and $R_2$ and $R_3$ are H are derived from thiols of formula

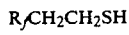

where $R_f$ is a perfluoroalkyl of 6 to 12 carbon atoms, and epichlorhydrin, namely 3-(1,1,2,2-perfluoroalkylthio)-1,2-epoxypropanes

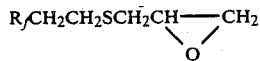

In one embodiment, the amino acid has the formula

where $R_4$ and $R_5$ are hydrogen or methyl, Z is a straight chain alkylene of 12 to 3 carbon atoms substituted by a carboxy or sulfo group and the acid adduct, alkali salt or N-lower alkyl quaternary ammonium salts thereof. In a preferred embodiment $R_4$ is methyl.

The amino acids of use in this invention include both naturally occurring and synthetic amino acids containing not only the common carboxy and sulfo substituents but also sulfate, phosphoro and phosphono groups. These include glycine, alanine, valine, leucine, isoleucine, phenylalanine, proline, methionine, serine, threonine, cysterine, tyrosine, tryptophan, aminoadipic acid, alanine, methylalenine, aminobutyric acid, ethylglycine, norvaline, aspartic acid, sarcosine, iminodiacetic acid, aminobenzoic acid, 2-aminoethyl hydrogen sulfate, 2-aminoethylthiosulfuric acid, 2-aminoethyl hydrogen phosphate, taurine, methyl taurine.

The addition of epoxide to amino acid is a base catalyzed reaction which occurs most readily in a single phase. This is generally provided in an aqueous solvent mixture by choice of a suitable water miscible cosolvent such as methanol, isopropanol, butoxyethanol and the like. The reaction is generally conducted at temperatures from 25° to 200°, but preferably from 50° to 130°.

The reaction can be run uncatalyzed if the reactant is sufficiently basic or at an alkaline pH provided by alkali hydroxide, ion-exchange catalyst or a non-reactive base, e.g. triisopropylamine.

The products are generally useful without isolation but can be isolated depending on the pH, in acid foam, as isoelectronic neutral salts or as alkali metal or ammonium salts. The fully quaternized derivatives containing N-lower alkyl or N-benzyl quaternary functions are generally isolated as neutral zwitterionic compounds or acid adducts, e.g. hydrochlorides.

The subject amphoteric compounds are very stable to hydrolysis and find numerous uses as surfactants and wetting agents. Since they are derived from readily available amino acids and certain readily available fluorinated epoxides they comprise particularly useful compositions.

EXAMPLE 1

A 50-ml flask was charged with 3-(1,1,2,2-tetrahydroperfluoro decanethio)-1,2-epoxypropane (5.4 g; 10 mmoles), sarcosine (1.0 g; 10.5 mmoles), 50% sodium hydroxide (0.9 g; 11 mmoles), isopropanol (18 g) and sufficient water (5 g) to attain a clear solution. The solution was heated to 77° C. for 5 hours. After cooling, the solvent was removed by evaporation and the recovered solids were redissolved in water. The insolubles were filtered off, the filtrate dialyzed for 72 hours, and the product recovered by evaporation.

Analysis: Calculated for $C_{16}H_{16}F_{17}NO_3S$; C, 30.8; H 2.4; N 2.2. Found: C, 30.0; H, 2.3; N, 1.8.

EXAMPLE 2

A 50-ml flask was charged with 3-(1,1,2,2-tetrahydroperfluorooctanethio)-1,2-epoxypropane (3.0 g; 6.9 mmoles), aspartic acid (1.0 g, 7.2 mmoles), 50% sodium hydroxide (0.6 g, 7.5 mmoles), isopropanol (12.6 g) and sufficient water (19.2 g) to attain a clear solution. The solution was heated to 70° C. for 24 hours. After cooling, the solvent was removed by evaporation and the recovered solids were redissolved in water. The insolubles were filtered off, the filtrate dialyzed for 72 hours, and the product recovered by evaporation.

Analysis: Calculated for $C_{15}H_{14}F_{13}NNaO_5S$: C, 28.1; H, 2.5; N, 2.5. Found C, 29.7; H, 2.6; N, 2.0.

EXAMPLE 3

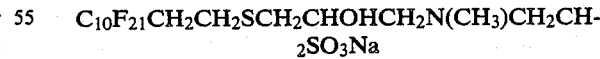

A 50 ml flask was charged with 3-(1,1,2,2-tetrahydroperfluorododecanethio)-1,2-epoxypropane (6.30 g; 10 mmoles), N-methyltaurine (6.21 g; 15 mmoles), 25% sodium hydroxide (0.10 g; 20 mmoles) and 20 g of methanol. The solution was heated to 75° C. for 16 hours. After cooling, 100 ml of water and 400 ml of methanol were added, the solution filtered at 72° C., cooled to 0°–10° C. refiltered and dried in vacuo at 70° C.

Analysis: Calculated for $C_{18}H_{17}F_{21}NNaO_4S_2$: C, 27.1; H, 2.2; N, 1.8; F, 50.0; S, 8.0. Found: C, 27.2; H, 2.2; N, 1.3; F, 52.3; S, 7.5.

EXAMPLE 4

A 50 ml flask was charged with 3-(1,1,2,2-tetrahydroperfluorododecanethio)-1,2-epoxypropane (6.30 g; 10 mmoles), iminodiacetic acid (2.93 g, 15 mmoles), 25% sodium hydroxide (3.20 g; 20 mmoles) and 20 g of methanol. The reaction mixture was heated to 75° C. for 16 hours. After cooling, it was acidified with hydrochloric acid, filtered, washed with methanol and dried in vacuo at 70° C.

Analysis: Calculated for $C_{19}H_{16}F_{21}NO_5S$: C, 29.7; H, 2.1. Found: C, 28.7 ; H, 2.1 (Nitrogen analysis inconsistent).

'-NMR was consistent with the product structure: δ 2.35 (2H, m) $CF_2\underline{CH_2}$; δ 2.72 (4H, m) $CF_2CH_2\underline{CH_2}S\underline{CH_2}$; δ 3.36 (2H, S) $NH\underline{CH_2}CO_2^-$; δ 3.43 (2H, S) $NH\underline{CH_2} CO_2H$, δ 3.49 (2H) $\underline{CHOH}\underline{CH_2}NH$; δ 3.27 (1H, Quintet) $CHO\underline{H}$.

EXAMPLE 5

A 50 ml flask was charged with 3-(1,1,2,2-tetrahydroperfluorododecanethio)-1,2-epoxypropane (6.30 g; 10 mmoles), aspartic acid (2.0 g; 15 mmoles), 25% sodium hydroxide (3.2 g; 20 mmoles) and 20 g of methanol. The reaction mixture was heated to 75° C. for 16 hours. After cooling, it was acidified with hydrochloric acid, filtered, cooled to 0°-10° C., refiltered and dried.

Analysis: Calculated for $C_{19}H_{16}F_{21}NO_5S$: C, 29.7; H, 2.1; N, 1.8. Found: C, 28.7; H, 1.8; N, 1.1.

'H-NMR was consistent with the product structure: δ 2.34 (2H, m) $CF_2-\underline{CH_2}$; 2.71 (6H, m) $\underline{CH_3}-S-\underline{CH_2}$, $\underline{CH_3}CO_2H$; δ 3.53 (5H, m) $\underline{CH_2}-N^+-\underline{CH_2}$, $CH\underline{OH}$

EXAMPLE 8

Several of the more water soluble $C_6$ surfactants functioned well as surface tension depressants in N/10 sodium hydroxide.

| Example | Surface Tension (dynes/cm) | |
| --- | --- | --- |
| | 0.01% | 0.001% |
| $2^a$ | 17.8 | 34.5 |

[a] This surfactant was pre-wetted with ethanol to hasten solubility.

What is claimed is:

1. A perfluoroalkyl thioalkylene amphoteric compound of the formula $$R_f-R_1-SCH_2CR_2(OH)CHR_3NR_4R_5Z$$

$R_f$ is straight or branched chain perfluoroalkyl of 6 to 12 carbon atoms or said perfluoroalkyl substituted by perfluoroalkoxy of 2 to 6 atoms;

$R_1$ is branched or straight chain alkylene of 2 to 8 carbon atoms, alkylenethioalkylene of 2 to 8 carbon atoms, alkyleneoxyalkylene of 2 to 8 carbon atoms or alkyleneiminoalkylene of 2 to 8 carbon atoms where the nitrogen atom contains hydrogen or alkyl of 1 to 6 carbon atoms as a third substituent;

$R_2$ and $R_3$ are independently hydrogen or lower alkyl from 1 to 6 carbon atoms, lower alkoxyalkyl, halo loweralkyl, cycloalkyl of 5 or 6 carbons and alkenyl of up to 6 carbon atoms;

$R_4$ and $R_5$ are independently hydrogen or straight or branched chain alkyl of 1 to 12 carbon atoms or phenyl which are unsubstituted or substituted by carboxy, sulfo, sulfato, phosphoro or phosphono; and Z is straight or branched chain alkylene of 1 to 12 carbon atoms which is substituted by carboxy, sulfo, sulfato, phosphoro, or phosphono, or thiosulfato and the acid adduct, alkaline salt, or N-lower alkyl or N-benzyl quaternary ammonium salts thereof.

2. A compound according to claim 1, wherein $R_f$ is straight or branched chain perfluoroalkyl of 6 to 12 carbon atoms or said perfluoroalkyl substituted by perfluoroalkoxy of 2 to 6 atoms;

$R_1$ is branched or straight chain alkylene of 2 to 8 carbon atoms, alkylenethioalkylene of 2 to 8 carbon atoms, alkyleneoxyalkylene of 2 to 8 carbon atoms or alkyleneiminoalkylene of 2 to 8 carbon atoms where the nitrogen atom contains hydrogen or alkyl of 1 to 6 carbon atoms as a third substituent;

$R_2$ and $R_3$ are hydrogen;

$R_4$ and $R_5$ are hydrogen, methyl, or alkyl substituted by carboxy;

Z is alkylene of 1 to 3 carbon atoms substituted by carboxy or sulfo; and the acid adduct, alkaline salt or N-lower alkyl quarternary ammonium salts thereof.

3. A compound according to claim 1, wherein $R_f$ is perfluoroalkyl of 6 to 12 carbon atoms;

$R_1$ is alkylene of 2 to 4 carbon atoms;

$R_2$ and $R_3$ are hydrogen;

$R_4$ and $R_5$ are hydrogen or methyl, or lower alkyl substituted by carboxy;

Z is alkylene of 1 to 3 carbon atoms substituted by carboxy or sulfo; and the acid adduct, alkaline salt or N-lower alkyl quaternary ammonium salts thereof.

* * * * *